United States Patent [19]
Robinson

[11] Patent Number: 5,918,266
[45] Date of Patent: Jun. 29, 1999

[54] METHOD AND APPARATUS FOR NON-DESTRUCTIVE MEASUREMENT OF FIRMNESS INDEX AND CALCULATION OF FIRMNESS

[76] Inventor: Alfred Vern Robinson, 68705 E. 715 PRNE, Richland, Wash. 99352

[21] Appl. No.: 08/971,060

[22] Filed: Nov. 14, 1997

[51] Int. Cl.⁶ .............................. G01B 13/08; G01N 9/00
[52] U.S. Cl. .............................. 73/37.5; 73/573; 73/818; 209/599
[58] Field of Search ................. 73/37, 37.5, 81, 73/579, 573, 709, 818; 209/599

[56] References Cited

U.S. PATENT DOCUMENTS

| | | | |
|---|---|---|---|
| 4,061,020 | 12/1977 | Fridley et al. | 73/81 |
| 5,152,401 | 10/1992 | Affeldt, Jr. et al. | 209/556 |
| 5,315,879 | 5/1994 | Crochon et al. | 73/818 |
| 5,372,030 | 12/1994 | Prussia et al. | 73/268 |
| 5,593,714 | 1/1997 | Hirsch | 426/268 |
| 5,691,473 | 11/1997 | Peleg | 73/573 |

OTHER PUBLICATIONS

A Non–Destructive Firmness (NDF) Testing Unit for Fruit, American Society of Agricultural Engineers, 1977, 20/4, pp. 762–767, Perry, John S.

*Primary Examiner*—Hezron Williams
*Assistant Examiner*—Jay L. Politzer
*Attorney, Agent, or Firm*—Floyd E. Ivey

[57] ABSTRACT

A firmness measuring method and device for non-destructive testing of objects (such as fruits) is disclosed. The device comprises the following components: a means to affect the size and/or shape of the object(s) through application of a compressive force (such as increased liquid, fluid, or mechanical pressure); or an expansive force (such as decreased liquid, fluid, or mechanical pressure); a means to measure or infer the volumetric change of the object(s) caused by application of the force; and/or measurement of surface deformation; an analyzer to utilize the volume change and/or amount of deformation of the surface caused by the applied force to infer the firmness of the object(s); a controller to coordinate the application of force, the measurement of object(s) response and the inference of firmness or firmness. Inference of firmness may also use additional information on the object(s) such as harvest date, manufacture date, weight, variety, chemical concentration, or water content.

7 Claims, 3 Drawing Sheets

METHOD AND APPARATUS FOR NON-DESTRUCTIVE MEASUREMENT OF FIRMNESS INDEX AND CALCULATION OF FIRMNESS

BACKGROUND OF THE INVENTION

1. Field of the Invention

The present invention relates to a device and a method for determining the firmness of one or more objects, and more particularly to a device and method for non-destructively measuring the firmness of objects, and most particularly to a device and means for non-destructively measuring the firmness of objects using an application of force, with subsequent measurement (or inference) of (i) the volumetric change induced by the force and (ii) the weight (and/or density) of an object(s)(s) so as to determine the firmness of the object(s).

2. Description of Prior Art

As used herein, "firmness" is defined as resistance to deformation, and is a key factor in determining acceptability of a number of products, specifically the quality of food products such as fruits and vegetables. Consumers consider firmness as a predictor of the storing ability and eating quality of fresh fruits and vegetables. Food buyers use firmness when selecting which lot to purchase. Firmness is also a key factor for growers in deciding on harvest dates and in sorting products at packing houses. As used herein, "hardness" may also be used interchangeably with firmness.

One of the primary functions of a fresh fruit and vegetable packing house is to convert a highly variable incoming flow of a product into packages containing products with uniform quality. Many products continue to ripen after harvest, therefore the items packed must be firmer than desired by the end user. Thus, a critical operation of packing houses is to remove riper items which are often the highest quality and more valuable for regional markets but would become soft and cause wholesale buyers to reject the entire shipment when delivered to distant markets. In the apple industry, fruit firmness has long been recognized as an important factor in evaluating apple quality, Finney, Essex, Jr., "Dynamic Elastic Properties and Sensory Quality of Apple Fruit", Journal of Texture Studies 2 62–74 (1971).

Unacceptable variations in firmness frequently occur during food production, manufacturing processes, and product storage. A common method for minimizing variability and for marketing products with uniform firmness is to separate items into groups with similar firmness levels.

Presently, manual separation is the only practical method available to packing houses for firmness sorting. The sorting task is labor intensive, monotonous and inaccurate. Consequently, there is a strong need for development of a mechanical device to measure the firmness of objects during the packing process which will allow separation of objects based on that firmness.

There are several methods of measuring firmness. Generally, such methods measure firmness by destroying the item under test. With these methods, one randomly selects samples from a lot and measures them under the assumption that they represent the total population. The traditional measure of fruit firmness is to measure the force required to penetrate the flesh of the fruit with a penetrometer of standard configuration and tip size. This device destructively measures the firmness of an object by determining the maximum force necessary to penetrate the object with a probe to a predetermined depth. A recent discussion of various destructive test methods is found in a paper by Abbot et. al. (Abbot, J. A., Watada, A. E., Massie D. R., 1976. Effi-gi, Magness-Taylor, and Instron Fruit Pressure Testing Devices for Apples, Peaches, and Nectarines. J. Amer. Soc. Hort. Sci., 101(6):698).

A major disadvantage of destructive testing is that to achieve higher levels of reliability one must destroy greater numbers of the product, and one cannot measure the firmness of every item going through a packing line with destructive test procedures. Furthermore, the ability for a limited sample size (typically less than 0.5% of the total number of individual fruits) to predict the condition of the lot is further weakened because weather and other variables prevent the control of processes (temperature, water stress, nutrient status, etc.) which affect the variability of firmness from fruit to fruit. Thus a lot will have variations that are only partially reduced by mechanical or manual sorting based on size, variety and color. As the fruit ages the variability in the firmness of individual fruits increases and thus the ability to predict the condition of the lot degrades. This is particularly important in determining the time at which controlled atmosphere (CA) storage rooms are opened and once opened whether the fruit (e.g. apples) can be sold on the open market as fresh fruit or has to be diverted to processing. The economic impacts of those decisions are significant for the individual grower and the industry as a whole.

Destructive tests for firmness continue, largely because suitable sensors are not available for measuring the firmness of all items in a lot. Consequently, effort has been expended on several approaches for finding a non-destructive firmness testing method. Such methods have either required mechanical contact between the product and a solid probe or measurement of a secondary property which is subsequently correlated to firmness.

A discussion of the various approaches that have been pursued is provided in U.S. Pat. No. 5,372,030 (Dec. 13, 1994) by Prussia, Astleford and others from the University of Georgia and in U.S. Pat. No. 4,061,020 (Dec. 6, 1977) by Fridley, Chen and others from U.C. Berkley. The methodology in the two referenced patents are basically point compression methods which relate the compression of a point or a spot on the surface of the test object (fruit) to the firmness of the entire fruit. A common defect of the point compression technique and the instruments that would be based on this technique, is the fact that only a single point or at best a few points are measured. The point deformation methods typically use a hard ball or pin to deform the fruit at the measurement point.

Alternatively, the technique in U.S. Pat. No. 5,372,030 uses air to deform the fruit at the measurement point and a laser beam to measure the deflection, but it is still basically a point deflection method. It is well documented that the apple is not homogeneous in regard to firmness test results obtained from the destructive punch test firmness determination and would not be expected to be uniform with regard to point compression as a measure of firmness. Most researchers (Abbott, 1976, 1994) take multiple measurements on the apple in order to average out known variations. In the experiments conducted in support of the development of this patent application, it has been noted that with four destructive punch tests, the relative standard deviation of the four tests has been on the order of eight to ten percent (a variability of approximately. 1 to 2 lb. of compression per apple) although some apples exhibit up to 25% difference (>3 lb.) from one location on the apple to the other. This data is consistent with that of other researchers (Abbot, Judith A., "Firmness Measurement of Freshly Harvested 'Delicious' Apples by Sensory Methods, Sonic Transmission, Magness-Taylor, and Compression", J. Amer. Soc. Hort. Sci. 119(3):510–515, 1994) and illustrates that there is significant point to point deviation around the apple in the underlying property (firmness) that is being measured. The property that the consumer and the industry should be most interested in is the general or average firmness of the entire apple. However, other methods that are currently proposed as non destructive firmness measuring techniques typically make point measurements and extrapolate the results from that point measurement to the whole apple.

There is need for a method and apparatus that can test the individual object (e.g. apple) for the desired property of firmness. There is a further need to be able to test non-destructively, multiple objects as a group to obtain the average property of firmness without testing each individual object (e.g. apple). A variant of the apparatus may be used for testing individual objects on a production or processing line, for example apples on the packing line.

SUMMARY OF THE INVENTION

It is thus an object of the invention to provide a non-destructive method of directly testing the firmness of fruit and other objects that relates a change in all or substantially all of the object(s) volume to the desired property of firmness or firmness.

It is further an object of the invention to provide an efficient, non-destructive method for testing the firmness of fruit or other objects individually or as a group.

A still further object of the invention is to provide a non-destructive method for testing the firmness of objects having variable characteristics such as surface roughness, or highly variable density or shape. The application of a deforming force over a non-point area allows the application of more force without damaging the object(s) due to excessively high point pressures on knobs or high points on the test object(s). The application of the force over all or substantially all of the surface of the test object(s) maximizes the response (volume change) that is measurable when compared to point compression measurements. In addition the method inherently provides a more reliable average measurement of the desired property (firmness), precluding the need to extrapolate from point or small area measurements to the whole object(s).

To accomplish these and other objects, the subject invention non-destructively measures the firmness of food products and other items (e.g. racquet balls) where firmness is an indicator of quality, by deforming all or substantially all of the surface of the object(s) under test and using any of a variety of sensors including, machine vision, calculations, or secondary measurements to obtain the volume change of the object(s). The measured or inferred volume change is combined with additional variables such as weight, and variety (for fruit), and a firmness index is calculated which relates directly to the firmness of the object or objects. Some examples of other variables that may be combined with the induced volume change include weight, density, type of material (rubber, wood, fruit variety etc.), total dissolved solids, sugar, starch, and picking date (for fruit). Any suitable method may be used to effect a volume change in the test object(s). The volume change may be induced by changes in fluid pressure (e.g. air or water pressure), or other methods could be used (e.g. opposing fluid filled bladders, sonic shock waves, mechanical force, etc.).

This method has several advantages over the prior art. For example, the deformation force is distributed over all or substantially all of the test area of the surface of the object(s) as opposed to only the raised portions of an irregular or "bumpy" test area, as would a mechanical device, thus minimizing the damage to the tissues of the object(s) by distributing the applied pressure over a greater surface area rather than concentrating it at one or a few discrete points corresponding to the bumps. This device allows compressive force to be applied to all or substantially all of the surface of the test object(s), thus maximizing the measured response and providing an average of the whole object(s) in contrast to measurement at discrete points. The device can be constructed from commercially available components that are relatively inexpensive. A significant requirement in many firmness measuring devices is the orientation of the test object(s). In this device, orientation is not important since in its simplest form, it is only the weight and volume of the entire object(s) that is being measured or inferred. In a packing house operation that requires multiple tests per second this in an important attribute. The minimum necessary measurement inputs to calculate the firmness index and ultimately predict the firmness of the object(s) are weight and volume change. In current apple packing houses for instance, individual apple weight is already measured so the only additional information needed is a volume measurement with and without an application of force to the fruit and the subsequent calculation of the firmness index, which can then be used with current computer controlled equipment and algorithms to direct fruit to the appropriate area for labeling and packing.

By performing the inventive method on a number of items simultaneously, this method also is capable of measuring the average firmness of a batch of test objects. By measuring the weight and volume change of multiple test objects at the same time in a batch mode, decisions can be made on the gross average firmness of a batch of the test objects (e.g. apples) over time. Applicant is unaware of any other process that can perform such measurements. For example, this methodology could be used to remotely and cheaply measure over time the firmness of apples sealed in controlled atmosphere storage (the apples are not easily accessible while in controlled atmosphere or low oxygen storage) without physically accessing the test batch. By making repeated measurements of the bulk properties of a subset of the whole population of apples while in storage, the rate of softening could be predicted and the apples could be removed from storage, packed and sold before they were too soft for the commercial fresh fruit market.

DETAILED DESCRIPTION OF THE INVENTION

Figure 1:
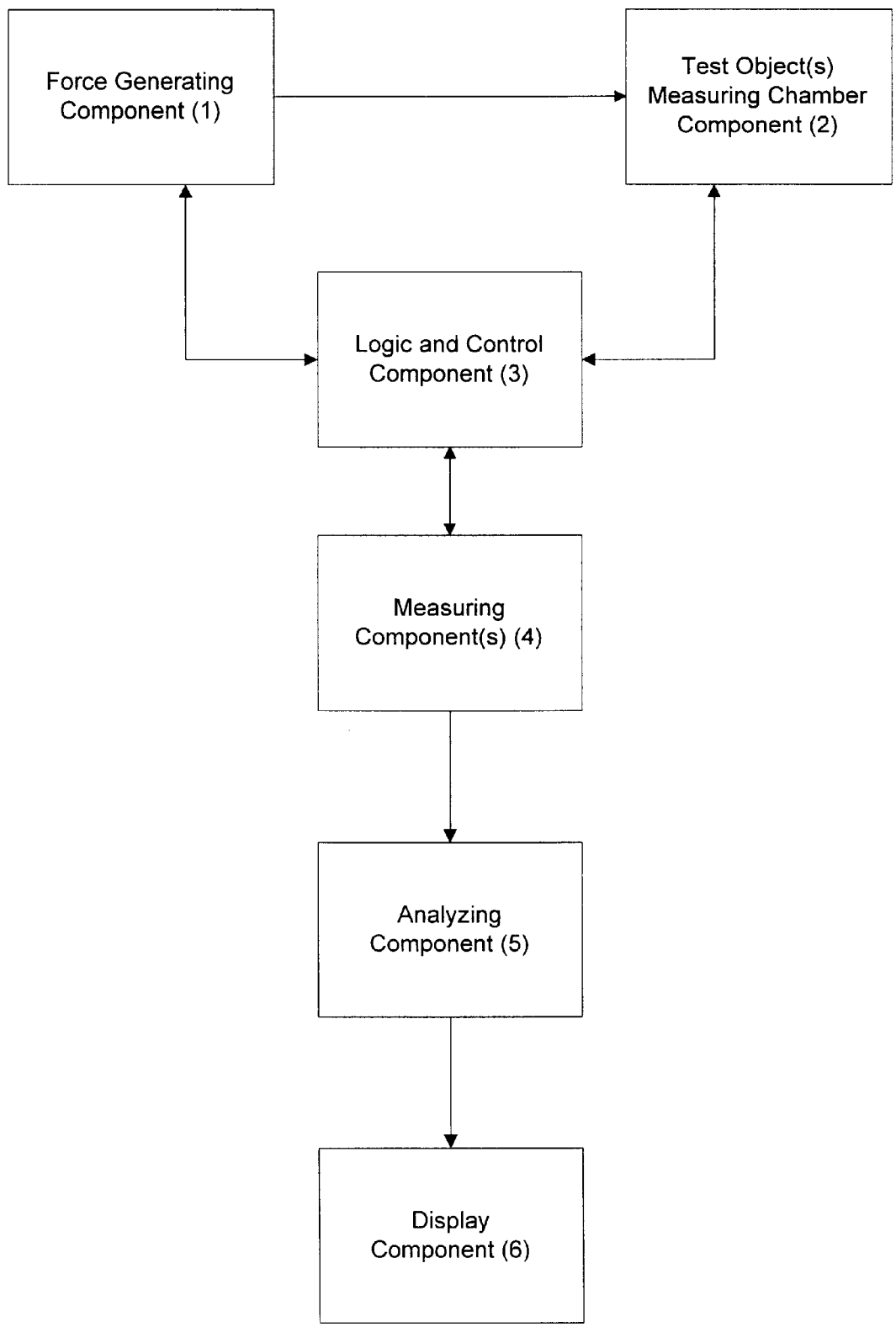
FIG. 1 is a block diagram of the basic components of the invention.

FIG. 1 is a generalized flow diagram of the claimed method. The Force Generating Component(1) can be any device capable of generating a deforming force over all or substantially all of the surface of the test object(s). The force that is generated by the Force Generating Component(1) is transferred via the appropriate linkages to the test object(s)

in the Test Object(s) Measuring Chamber(2). The Test Object(s) Measuring Chamber(2) is capable of receiving the test object or objects and is configured to allow the application of the force to the test object(s). The Logic and Control Component(3) controls the starting and stopping of the force generation and the suitable switches and valves to transfer force to the test object(s) in the chamber(2). The Logic Control Component(3) also controls timing so that application of the force, and measurement of the results of the application of force to the test object(s), occur in a predetermined sequence. The Measuring Component(s)(4) obtain data from sensors in the Force Generating Component(1) and Test Object(s) Measuring Chamber(2) and interacts with the Logic and Control Component(3) so that the various sensors are activated and interrogated to obtain data at the precise time it is available. The Measuring Component(s)(4) also receives and processes data from appropriate sensors and translates such data to a digital form for transfer to the Analyzing Component(5). The Analyzing Component(5) combines data from multiple sensors in one or more Measuring Components and performs calculations with the sensor data to obtain an estimated object(s) firmness.

The basic equation that is used in this inventive method is as shown below:

$$(V_{TO}-V_F)/[n*(W_O/V_{TO})^Z] = \text{Firmness Index} \qquad \text{Equation 1}$$

wherein $V_{TO}$=volume of the test object(s) in the absence of the applied force $V_F$=volume of the test object(s) during the application of the applied force $W_O$=Weight of the test object(s)

Z=dimensionless factor that can any real number, factor is determined empirically for each class of test objects.

n=number of test objects in the test chamber

The firmness index is then related to the desired property of the test object(s) through the use of a lookup table, correlation curve or mathematical expression of the relationship between the non-destructively measured firmness index and the desired property of the object(s). An example of this might include, for determination of apple firmness, the use of a calibration equation based on empirical data that relates the measured firmness index to the destructively measured pressure punch test results for a specific variety (Red Delicious apples, Golden Delicious apples, etc.) of fruit. The calibration equation can be stored in the Analyzing Component(5) and can be selected by user input prior to testing the fruit. It is anticipated that the use of additional variables to assist in the relation of the measured non-destructive firmness index to the desired property in the test object(s) may include, but are not limited to, chemical composition of the object(s), starch levels, sugar levels, time of manufacture, time of harvest, surface color, spectral properties, x-ray absorption properties, etc.

Several measurements may be useful for correlating the change in volume to the firmness of the object(s). These include but are not limited to, measuring the change in object silhouette area before a deforming force is initiated and comparing that area to the area of the object silhouette after application of the deforming force. Another measurement method that would be suitable would be the use of machine vision components in conjunction with volume or area measuring software. Still another example of a method to measure the volume change would be to introduce a known amount of marker gas into a known fixed volume (test chamber) containing the object(s) to be tested, measure the marker gas concentration, apply a compressive force such as air pressure and measure the marker gas concentration again. The difference in gas concentration can be related to the compression volume of the object(s) tested. A more direct method of calculating the initial and deformed volume of the object(s) to be tested would be to measure the volume of the gas that is required to deform the fruit to a given end point of pressure or vacuum.

Two other measurements which can be correlated to firmness are the rate at which the volume of an object(s) deforms as the deforming force is applied and the rate at which the volume recovers to its non deformed state after the application of the deforming force has ceased.

The measurement of volume change following application of a deforming force may also be accomplished using sensors that expose the object(s) under test to one or more forms or energy (e.g. ultrasound; magnetic fields; electromagnetic radiation, such as visible light; microwave radiation; neutron, gamma or x-ray radiation). The sensors may measure surface deflection, or they may measure the 2 dimensional area of a silhouette and infer volume change from these measurements, or the three dimensional volume of the object(s) may be measured or estimated directly for the objects under test.

A potential embodiment of the invention uses a predetermined air pressure to effect a volume decrease in the test object(s), in this example case an apple. The amount of volume decrease is determined by measuring the decrease in the cross sectional area of the apple. The cross sectional area of the apple is measured by projecting a light at the apple from one side and measuring the light intensity by measuring the voltage or current output of an array of solar cells or using a light intensity meter. If the meter is used then the light could be collected via a lens system into a spot slightly less than the active area on the meter.

The intensity of the light (or sensor output voltage or current) before pressure is applied will be proportional to the original area of the fruit and the intensity of the light after the pressure is applied will be proportional to the area of the test fruit under the compressive force of the air pressure. These area changes are then used to estimate volume change and calculate the firmness index which is correlated to the firmness of the object(s). Although in some instances this could be done by direct calculation, determining the firmness of a particular class of objects as a function of volume deformation may also be done through empirical testing. After a sample of sufficient size has been tested, a standard table of firmness versus volume deformation can be created. Once this has been accomplished, firmness can then be determined by correlating the amount of volume deformation of the object(s) under test to its firmness, such as by curve-fitting techniques, manual or table-lookup, possibly with interpolation.

The volume change can be directly displayed by the inventive apparatus, which would allow one either to calculate a firmness index directly or to look up the firmness of the object(s) under test in a table which lists firmness as a function of firmness index. Alternately, the displacement signal can be supplied in analog or digital form to a firmness indicating device, suitably calibrated to transform the supplied signal into a display indicative of the firmness measurement. Automatic means such as a digital computer can also be used by supplying the displacement signal in a form suitable for input into the computer (e.g. a digital signal). The computer can then automatically perform the calculations necessary to compute firmness (for fruit firmness would correlate to the measured firmness in a known way, perhaps determined empirically-for each particular type of fruit) and display it in a suitable fashion, or control automatic processing and/or packing equipment.

This device can be employed as a fixed unit for firmness testing in a packing house or a factory. In a packing house it can be used to sort fruits and other food products on line during the sorting and packing process. It can test the firmness of the fruit on line, correlate the measured firmness index with firmness of the fruit (or some other predetermined property of the fruit or quality parameter), and then provide an input to devices or systems which place the fruit in a pre selected location based on its firmness.

It could also be employed as a bench-top tester used in a factory or packing house for process control. In this application it will be used for random sampling of the output of line sorters for quality control and line calibration. It could also be used as a bench-top tester used in a packing house or factory for product receiving inspections and to provide information used to determine processing disposition.

It could also be employed as a portable unit for firmness testing in the field of food products (e.g. as a table top or hand held device used to determine optimal fruit harvest time) or other products where firmness is an important factor (e.g. racquet balls used in tournament play).

A first embodiment of the invention comprises a pressure tight box with hinged lid (Test Object(s) Measurement Chamber(2)). It is to be understood that while the preferred embodiment disclosed herein comprises a positive pressure vessel the invention in its broadest sense can comprise any pressure generating apparatus that causes a physical deformation of the test object(s). For example, the pressure can be a negative pressure generated by a vacuum pump. The box and lid assembly are constructed to contain, for example, 100 psi. Inside the box is a weighing unit (Measurement Component(s)(4), comprised of a load cell and device for holding the apple upon which the apple (or other object) is placed. When the lid is closed, the weight of the apple is recorded and the data is stored in the Analyzing Component (5) for later use. The Force Generating Component(1) (for example a $CO_2$ cylinder or other compressed gas source) is affixed to a vessel of known volume that is pressurized to a predetermined level and is referred to as the supply pressure unit in the discussion below. A stream of compressed gas (such as air or $CO_2$) from the supply pressure unit is directed into the sealed Test Object(s) Measurement Chamber(2) until the pressure in the measurement chamber reaches a predetermined set end point, at which time the gas stream is turned off by the Logic and Control Component(3). In this embodiment, an estimate of the uncompressed volume of the apple is obtained by measuring the pressure in the Force Generating Component(1) when the applied pressure in the Test Object(s) Measurement chamber(2) has changed from 0 psi to some measurable level such as 1–5 psi. Inherent in this estimate of initial volume in this embodiment is the assumption that the compression of the test object(s) is negligible at low pressures compared to the final measurement pressures used. The estimate of volume in this embodiment is obtained by using a mathematical derivation of the universal gas law equation, $$PV=nRT \qquad \text{Equation 2}$$

Where
P=pressure of the gas in atmospheres
V=volume occupied by the gas in liters
n=moles of gas in volume V R=universal gas constant
T=temperature of the gas in degrees Kelvin By measuring the pressure and temperature of the gas in the two chambers and knowing the initial volume of the two chambers, the volume of the test object(s) (in this example an apple) in the Test Object(s) Measurement Chamber(2) can be estimated via the equation below.

$$V_{test\ object(s)}=V_{TMC}-V_{void} \qquad \text{Equation 3}$$

Where
$V_{test\ object(s)}$=Volume of the test object(s)
$V_{TMC}$=Volume of the empty Test Object(s) Measurement Chamber(2)
$V_{void}$=Volume of the Test Object(s) Measurement Chamber(2) not occupied by the test object(s)

A second estimate of volume is then obtained by recording the pressure in the Force Generating Component(1) when the pressure in the Test Object(s) Measurement Chamber(2) is at a predetermined level such as 40 psi. The Test Object(s) Measurement Chamber(2) is then vented to the atmosphere by the Logic and Control Component(3), returning the Test Object(s) Measurement Chamber(2) to atmospheric pressure. The Analyzing Component(5) in this example embodiment will use the measured pressure changes to calculate a volume reduction using equations 2 and 3 and, in conjunction with the object(s) weight, and the empirical factor Z, calculate a firmness index according to equation 1. The Analyzing Component(5) in this example embodiment would be a simple computer containing a lookup table relating the calculated firmness index to an estimated destructive pressure test firmness result. The estimated property of firmness for the apple would be displayed as a visual digital readout in the Display Component(6).

The Logic and Control Component(3) and the Analyzing Component(5) in this embodiment comprise of a dedicated computer board with the ability to control the switching on and off of the load cell (4), acquisition and electronic storage of the weight from the load cell, and electronic storage of the pressure data from the pressure measurement and switching unit, electronic storage of tables of calibration data, and data output for control of valves and switches in the Measuring Component(s)(4) as necessary.

The Measuring Components(4) in this embodiment comprises two electronic pressure sensors, power supply and ancillary fittings. The combined Analyzing Component(5) and Logic and Control Component(3) contains the electronics to control the switching on and off of appropriate valves and receive and transmit signals from the sensors, valves and switches. The combined(3,5) unit will control valves and switches according to predetermined sequences. These valves and switches will control the introduction of gas into the test chamber to predetermined pressure levels and subsequent venting of the working gas.

A second example embodiment of the invention comprises a pressure tight vessel with removable top as the Test Object(s) Measurement Chamber Component(2). The pressure vessel is constructed to contain 100 psi. The top of the pressure vessel is fitted with a volume calibrated column that can be vented to the atmosphere and is also fitted with a pressure gauge and air hose fitting so that the column can be pressurized by air from the Force Generating Component(1). Inside the vessel is a holder upon which the apple (or other object(s)) is placed. When the lid is closed a stream of liquid (such as water) is directed into the pressure vessel through a valve and fitting. The liquid serves as a means to transfer the force supplied by the air pressure to the object(s)

immersed in the water. The vent is left open and as the chamber fills, the liquid rises to a predetermined level in the calibrated column, at which point the introduction of liquid ceases and the vent is closed. Pressurized air is now directed into the top of the column through the air hose fitting until the pressure of the air in the column reaches a predetermined set point, at which time the gas stream is turned off manually. An estimate of the compression volume of the test object(s) is then obtained by recording the initial liquid level (before application of pressure) on the calibrated tube and subsequently recording the liquid level after the application of the predetermined pressure. The compressed volume of the test object(s) is calculated by converting the difference in liquid heights in the column to the volume represented by that difference. The air above the liquid in the column is then vented to the atmosphere by a vent valve in the top of the column), allowing the Test Object(s) Measurement Chamber Component(2) to return to atmospheric pressure. The manual calculation of object(s) firmness (in this case an apple) will use the measured volume reduction in conjunction with the initial volume and weight of the object(s) obtained separately to calculate a firmness index and subsequent estimated firmness.

In a third example embodiment of the invention, the Test Object(s) Measurement Chamber Component(2), comprises a pressure tight box with removable top that is large enough for the introduction of multiple objects (in this example, apples). The pressure tight box could be any shape or volume that is required for a specific application. In this embodiment, the box will have enough free internal volume to contain the contents of a standard apple box (approximately 35–45 lb. of apples). The pressure vessel will have a means to circulate the air up through the bottom of the apples in the box as well as a small pump and a device to inject a precisely known volume of gas. The apples will be placed in the box and the box will be sealed just prior to a measurement sequence. In this embodiment of the invention, the initial volume of the fruit will be established by an injection of a known quantity of gas (possibly $CO_2$) into the sealed vessel containing the fruit. After a predetermined time of circulating the gas in order to allow equilibration with the void volume (pressure vessel volume—apple volume) the concentration of the injected gas in the headspace of the pressure vessel will be measured via a sensor and compared to a reference measurement performed in the pressure vessel prior to the introduction of the tracer gas. The pressure inside the box will then be increased by a small pump injecting air to preset pressure levels and the concentration of $CO_2$ in the pressure vessel will be measured as before with the gas sensor. The volume of air that is required to accomplish that pressure change will be recorded.

The control of injection of gas, control of valves and time sequences, and venting of gas pressure will be performed by the Logic and Control Component(3). The signal processing from the sensors discussed above, calculation of bulk firmness index and comparison to a lookup table of apple firmness versus bulk firmness index will be performed by the Analyzing Component(5), which in this case is a microprocessor with appropriate software and memory capabilities. In this example embodiment of the invention, it is assumed that the number of apples and the weight of the apples that are placed in the box are previously obtained with separate devices and the data is entered into the Analyzing Component(5). The data will be displayed by the Display Component(6) which in this example will consist of a transmitting device capable of transmitting the final estimated property of average apple firmness and ancillary data such as the firmness index, number of apples, identification of sample lot to a receiving computer for storage and manipulation at a location remote from the firmness tester.

The data used in the calculations will consist of the weight of the apples in the box (supplied by the user), the number of apples in the box (supplied by the user), the initial volume of the apples (measured), the volume of the apples after the application of the pre determined pressure (measured), and the apple variety. The Analyzing Component(5) will calculate the estimated average firmness for the entire batch of fruit and display the result via the Display Unit(6).

EXAMPLE

Figure 2:
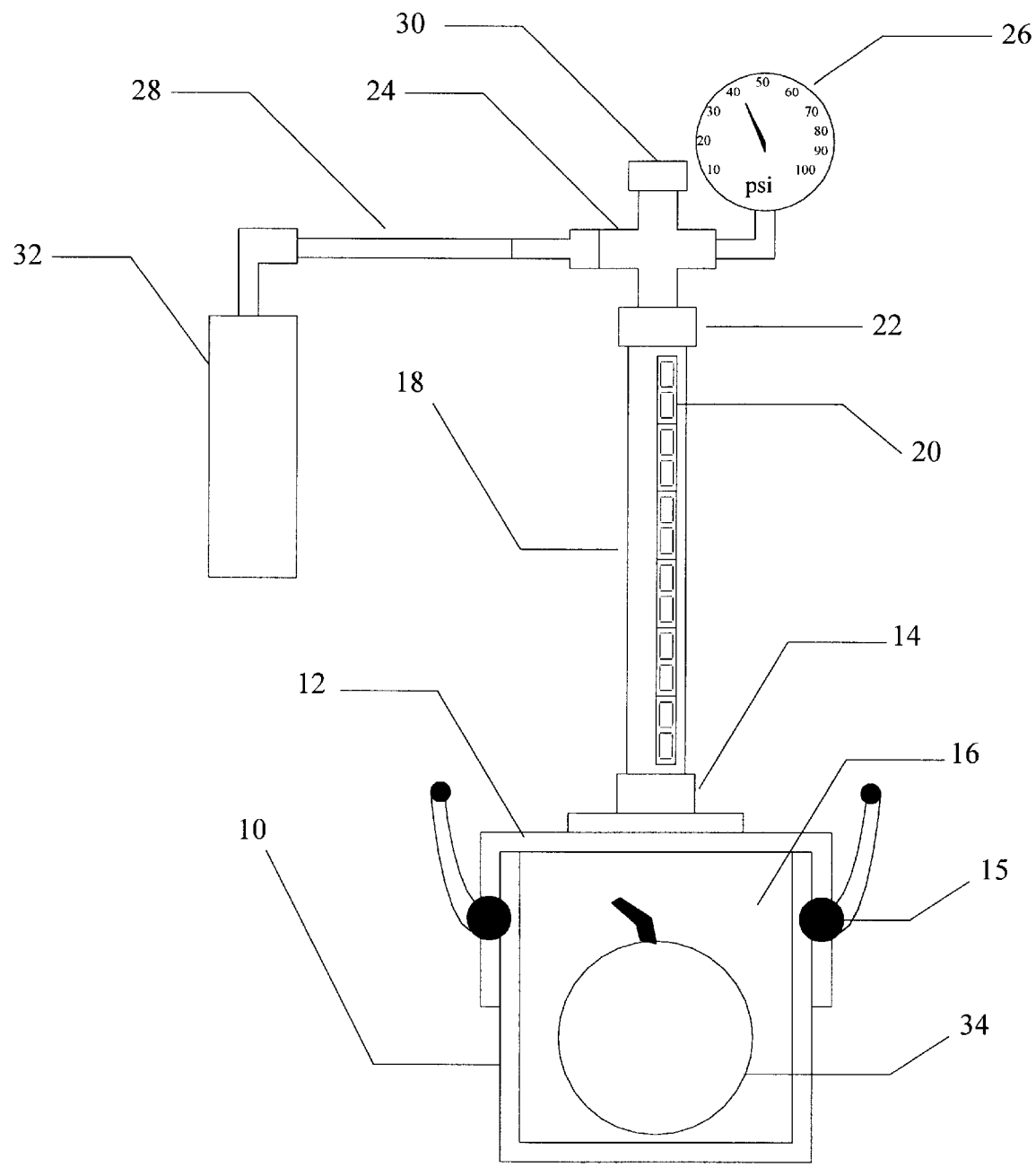
FIG. 2 is a schematic drawing of the apparatus used to demonstrate the inventive method and generate the data illustrated in FIG. 3 below.

In one embodiment of the method, a group of 9 Red Delicious apples obtained from a local grocery store were tested non-destructively via the inventive method described above. A drawing of the apparatus that was used to demonstrate the inventive method is shown schematically in FIG. 2 and discussed below. As shown in FIG. 2., the cylindrical measurement chamber base(10) was comprised of a 4 inch male tube fitting and the cylindrical measurement chamber cap(12) was a 4 inch female cap threaded with four inch female pipe threads. The four inch thread in the female cap(12) was reduced a 1 inch male thread(14) with standard pipe fittings. The measurement chamber cap(12) and base (10) are capable of being sealed together by latches(15) to form a measurement chamber(16). The measurement chamber(16) is capable of containing more than 100 psi when assembled. The top of the measurement chamber(16) was fitted with a ¾ inch inside diameter translucent tube (18), hereafter called a column, attached to the 1 inch male thread(14). A millimeter ruler(20) was attached to the ¾ inch column(18) and the column terminated in a one inch female thread(22). The top of the column (18) was fitted with a ½ inch PVC cross tee(24), pressure gauge(26), air hose(28), and cap(30). The column(18) was pressurized through the air hose(28) by air from the Force Generating Component (32), in this case a passive air pressure tank pressurized to 60–80 psi. The column(18) was vented to the atmosphere through the cap(30) or air hose(28) as needed. The apple(34) was placed inside the measurement chamber(16) and a stream of water was directed into the measurement chamber (16) through the cap(30) on the top of the column(18). The water served as a means to transfer the force supplied by the air pressure to the apple immersed in the water. The liquid was filled to a predetermined level in the column(18) and the level on the millimeter ruler(20) was recorded, at which point the introduction of liquid ceased and cap(30) on the top of the testing unit was replaced. Air was now directed into the top of the column(18) through the air hose(28) from the pressure tank(32) until the pressure of the air in the column (18) reached a predetermined set point (5–70 psi), at which time the air stream was turned off manually. The liquid level (on the millimeter ruler) was recorded after the application of the predetermined pressure. The compressed volume of the apple was calculated by converting the difference in liquid levels in the column(18) (as measured by the millimeter ruler(20)) to the volume of water represented by that difference. The air above the liquid in the column(18) was then vented to the atmosphere through the cap(30), allowing the inventive apparatus to return to atmospheric pressure. The manual calculation of a firmness index for the apple used the measured volume reduction of the apple in conjunction with an estimate of the initial volume of the apple obtained by measuring water displacement in a separate apparatus, and the weight of the object obtained via a separate apparatus, to calculate a firmness index via equation 1. Previous experiments had suggested a value of Z=2 in equation 1. That Z value was used to calculate a firmness index for the 9 apples being tested.

Following non-destructive testing by the inventive method in the apparatus above, the apples were destructively measured for firmness with an Effe-Gi type destructive punch tester. The punch tester records the maximum force (displayed in units of Newtons and pounds) that was required to force a standard 11 mm (outside diameter) tip 7 mm into the apple flesh. The skin over the test area was removed prior to testing. This type of tester and methodology are typical of that used by the apple industry in Washington State and elsewhere. Each apple was tested in four or more locations around the equatorial perimeter of the fruit. The average firmness as measured by the destructive punch tests was then calculated along with a standard deviation of the four measurements.

Figure 3:
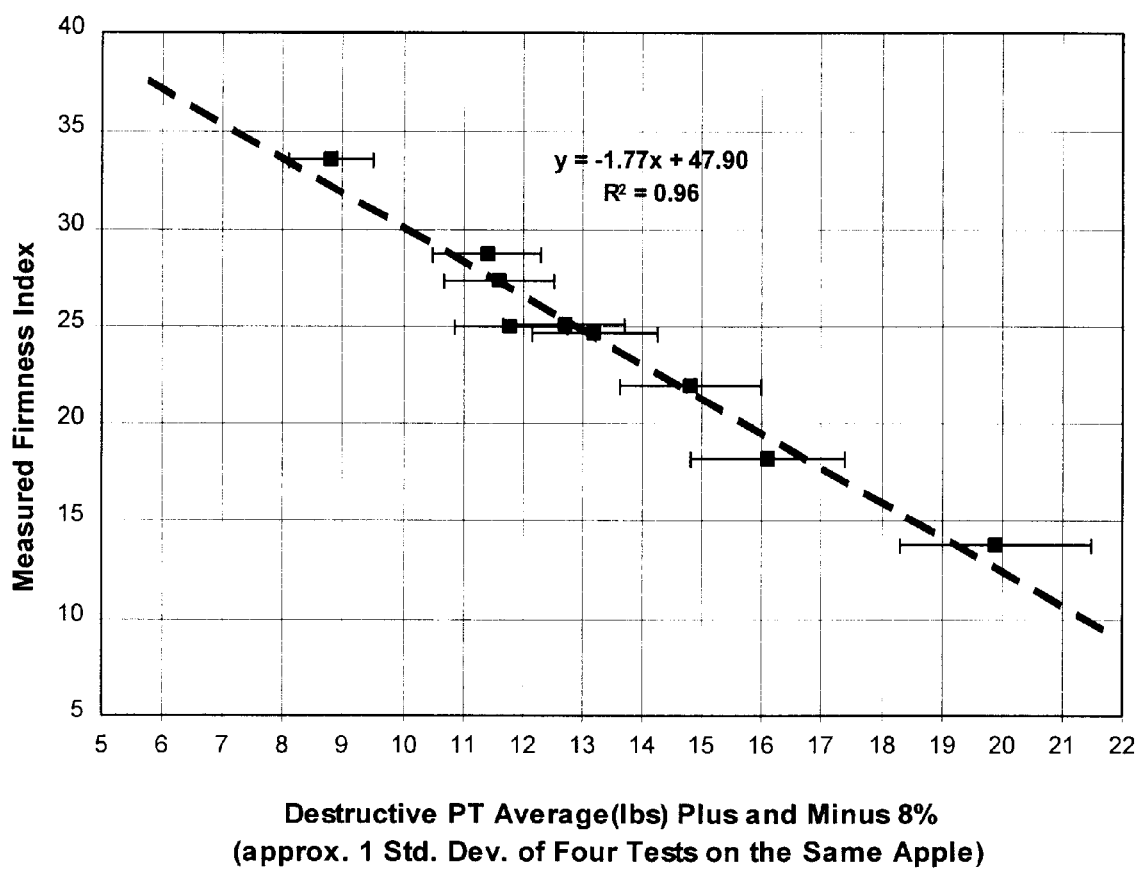
FIG. 3 is a graph illustrating the correlation between a non destructively determined firmness index by the inventive method and destructive test results of firmness.

A plot of the destructively measured firmness versus the calculated firmness index from the application of the inventive method, and Equation 1 via the apparatus shown in FIG. 2, was prepared and is shown in FIG. 3. A standard linear regression and curve fit were performed on the data and the resultant equation and correlation coefficient are displayed in the figure. As can be seen, there is a very strong correlation ($r^2$=0.96) between the non-destructively calculated firmness index and the actual destructively measured firmness. In almost all cases, the non-destructively predicted firmness is within one standard deviation of the measured firmness. It is important to note that in general the industry does not test each apple in four locations (one or two locations are typical) thus the current invention has the capability of allowing more tests per batch of apples by virtue of it being nondestructive thus providing a greater statistical certainty of the results. The current invention also provides a firmness estimate that factors in the entire apple surface, thus providing an average result that is closer to the actual average firmness for the fruit than a limited number of point measurements.

Preferred and alternative embodiments of the present invention have been disclosed herein. It is to be appreciated that those of skill in this art will be capable of making improvements and modifications of the invention which will fall within the spirit and scope of the present invention. Accordingly, the scope of the present invention should be determined solely by reference to the claims appended hereto.

What is claimed is:

1. A firmness measuring device for non-destructive testing of deformable test objects, comprising:
   a. a test object measuring chamber to receive the test object within which a force is applied to the test object;
   b. a force generating component to generate a deforming force that can be applied uniformly over all or substantially all of the surface area of the test object;
   c. a measuring component to
      (i) determine the magnitude of the deforming force and the variation of the deforming force
      (ii) measure the initial volume of the test object before application of the deforming force,
      (iii) measure the volume of the test object after application of the deforming force;
      (iv) measure the weight or density of the test object before and after the application of the deforming force;
      (v) measure the rate of deformation of the volume of the test object in response to the deforming force, and (vi) response to the deform force and
      (vi) measure the rate of recovery of volume of the test object after the application of the deforming force has ceased,
   d. an analyzing component responsive to a signal generated by the measuring component to compare the variables in (i) through (iv) above to determine the firmness of the object under test;
   e. a logic and control component to control the variables of (i) through (iv) above.

2. A method of non-destructively determining the firmness of a test object(s) comprising the steps of:
   a. changing the volume of the test object(s) by the application of a force to all or substantially all of the surface area of the test object(s)
   b. measuring the change in volume of the test object(s);
   c. measuring the weight of the test object(s) before and after changing the volume of the test object(s);
   d. correlating a change in volume to a firmness measurement of the test object(s);
   e. using the firmness measurement to select test objects meeting a pre selected firmness measurement criteria.

3. The method of claim 2, further comprising the step of correlating one or a plurality of variables, including weight, variety, density, type of material, total dissolved solids, sugar, starch, and picking date, average firmness, volume change, gross average firmness, rate of softening and object (s) firmness, chemical composition, time of manufacture, time of harvest, surface color, spectral properties and x-ray absorption properties, to the change in volume to determine a firmness measurement.

4. The method of claim 2 further comprising determining the firmness measurement according to the following equation:

$$(V_{TO}-V_F)/[n*(W_O/V_{TO})^Z]$$

where $V_{TO}$=volume of the test object(s) in the absence of the applied force;

$V_F$=volume of the test object(s) during the application of the applied force;

$W_O$=weight of the test object(s);

Z=dimensionless factor that can be any real number, factor is determined empirically for each class of test objects;

n=number of test objects in the test chamber.

5. The method of claim 2, further comprising inducing a positive pressure around the entire surface of the test object (s) to reduce the volume thereof.

6. The method of claim 2, further comprising drawing a vacuum around the test object(s) to increase the volume thereof.

7. The method of claim 2, further comprising removing from a quantity of test object(s) those test objects that fail to exhibit a firmness measurement meeting the pre-selected firmness measurement.

* * * * *